United States Patent
Mizutani et al.

(10) Patent No.: US 7,083,843 B2
(45) Date of Patent: Aug. 1, 2006

(54) TOP SHEET FOR ABSORBENT ARTICLES, AND METHOD FOR PRODUCING IT

(75) Inventors: Satoshi Mizutani, Kagawa (JP); Yuuki Noda, Kagawa (JP); Tatsuya Tamura, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 288 days.

(21) Appl. No.: 09/771,131

(22) Filed: Jan. 26, 2001

(65) Prior Publication Data

US 2001/0014796 A1  Aug. 16, 2001

(30) Foreign Application Priority Data

Feb. 2, 2000 (JP) ........................... 2000-025116

(51) Int. Cl.
*A41B 13/02* (2006.01)

(52) U.S. Cl. ............... 428/143; 428/141; 428/147; 604/367; 604/370; 604/385.01

(58) Field of Classification Search .......... 428/141, 428/143, 147, 148, 149; 604/367, 370, 385.01, 604/371; 442/417
See application file for complete search history.

(56) References Cited

U.S. PATENT DOCUMENTS

| | | | | |
|---|---|---|---|---|
| 4,327,730 A | | 5/1982 | Sorensen | .................... 128/287 |
| 5,019,062 A | * | 5/1991 | Ryan et al. | .................. 428/137 |
| 5,207,962 A | | 5/1993 | Hovis et al. | ................. 264/145 |
| 5,660,788 A | * | 8/1997 | Gray et al. | .................. 264/504 |
| 5,853,846 A | * | 12/1998 | Clark et al. | .................. 180/167 |
| 5,955,187 A | * | 9/1999 | McCormack et al. | .... 428/315.5 |
| 6,277,104 B1 | * | 8/2001 | Lasko et al. | ................. 604/368 |

FOREIGN PATENT DOCUMENTS

| | | |
|---|---|---|
| EP | 0958802 A2 | 11/1999 |
| EP | 1110526 A2 | 6/2001 |
| EP | 1201213 A2 | 5/2002 |
| JP | 61056645 | 3/1986 |
| JP | 04-279160 A1 | 10/1992 |
| JP | 05-200065 | 8/1993 |
| JP | 9-505223 | 5/1997 |
| WO | WO 94/20054 | 9/1994 |
| WO | 95/13774 | 5/1995 |
| WO | 97/00656 | 1/1997 |
| WO | 98/29481 | 7/1998 |

OTHER PUBLICATIONS

English translation of JP 04–279160 (PTO 2005–2472).

* cited by examiner

*Primary Examiner*—Harold Pyon
*Assistant Examiner*—Alicia Chevalier
(74) *Attorney, Agent, or Firm*—Darby & Darby

(57) ABSTRACT

Provided is a top sheet for absorbent articles including a number of perforations for covering a liquid-receiving surface of an absorbent article. The top sheet is formed of a thermoplastic resin containing a particulate material. The top sheet is provided with fine convex portions of the particulate material on the surface thereof and a plurality of protrusions extending from the surface thereof, and the height of each protrusion from the surface is larger than that of each fine convex portion therefrom.

12 Claims, 3 Drawing Sheets

TOP SHEET FOR ABSORBENT ARTICLES, AND METHOD FOR PRODUCING IT

BACKGROUND OF THE INVENTION

1. Field of the Invention

The present invention relates to an absorbent article for diapers, sanitary napkins, pantiliners, incontinence pads, etc., and to a method for producing a top sheet of the absorbent article. More precisely, the invention relates to such an absorbent article of which the top sheet has a good feel, and to a method for producing the top sheet thereof.

2. Description of the Related Art

Recently, the absorbent articles are widely used for sanitary napkins, pantiliners, incontinence pads, disposable diapers and others for absorbing excretions. Such absorbent article generally comprises a liquid-pervious top sheet to face the skin of a wearer (the top sheet is also referred to as a body facing surface), a liquid-impervious back sheet (the back sheet is also referred to as a garment facing surface), and a liquid-absorbing layer sandwiched between the top sheet and the back sheet. Since the top sheet is directly contacted with the skin of a wearer, it is desired to have a good feel. In addition, since the top sheet directly receives excretions, it is preferable that liquid excretions hardly stay therein so that the top sheet itself hardly becomes stuffy and sticky.

For example, Japanese Unexamined Patent Publication (Kokai) No. Heisei 5-200065 discloses a surface member for absorbent articles, which has a fine convex-concave pattern (this convex-concave pattern is also referred to as an embossed pattern hereinafter) on the surface thereof. As having the fine embossed pattern, the surface member disclosed therein does not have a plastic-like feel, excretions which it has received can immediately pass through its surface, and it hardly becomes stuffy and sticky. Furthermore, International Unexamined Patent Publication (Kohyo) No. Heisei 9-505223 discloses a liquid-pervious, porous plastic web containing a particulate material. The web is formed into a top sheet for absorbent articles which is soft and has a little plastic-like feel.

However, these still have some problems. In case of the former, the surface member is not sticky in dry, but when wetted, it shall have powers of resistance to liquid flowing thereon owing to the embossed pattern, and results in keeping liquid in recesses of the embossed pattern on its surface. In case of the latter, the web does not become so sticky even when wetted, but its ability to significantly remove the sticky feel in wet is still unsatisfactory. In producing the web, the particulate material is added to a semi-molten resin. However, the web thus produced is problematic in that the particulate material often drops off from its surface in use.

SUMMARY OF THE INVENTION

An object of the present invention is to provide a top sheet for absorbent articles, which is not sticky and has a good feel even in wet, and also to provide a method for producing such a top sheet.

According to an aspect of the invention, a top sheet may include a number of perforations for covering a liquid-receiving surface of an absorbent article, wherein;

the top sheet is formed of a thermoplastic resin containing a particulate material, and the top sheet is provided with fine convex portions of the particulate material on the surface thereof and a plurality of protrusions extending from the surface thereof, and the height of each protrusion from the surface is larger than that of each fine convex portion therefrom.

In this case, the particulate material has, for example, a mean particle size of from 0.1 μm to 30 μm. Preferably, the thermoplastic resin contains at least two types of particulate material that differ from each other in the mean particle size by at least 9 μm. Also preferably, the amount of the particulate material to be in the thermoplastic resin that forms the top sheet is from 20 to 150 parts by weight relative to 100 parts by weight of the thermoplastic resin.

The mean particle size referred to herein is obtained by measuring the major diameter of each particle of the particulate material that comprises a number of particles, followed by averaging the resulting data.

The mean height of the protrusions from the surface of the top sheet falls, for example, between 0.05 and 1.0 mm. The mean height is obtained by measuring the height of each protrusion that extends from the surface of the top sheet, followed by averaging the resulting data.

Preferably, the top sheet has micropores that allow water vapor to pass through it.

The protrusions may be formed by mechanically stretching the top sheet, for example, by use of needles.

According to another aspect of the ivention, a method for producing a top sheet for absorbent article, may comprise;

(a) a step of mixing from 20 to 150 parts by weight of a particulate material with 100 parts by weight of a thermoplastic resin, followed by melt-extruding the resulting mixture to form a sheet material, and (b) a step of placing the sheet material on the surface of a perforating member, followed by vacuuming the sheet material through perforating holes of the perforating member to perforate the sheet material.

Preferably, the method may further comprise, before the step (b), a step (c) of partially stretching the sheet material by use of needles to form a number of protrusions.

DESCRIPTION OF THE PREFERRED EMBODIMENTS

Figure 1:
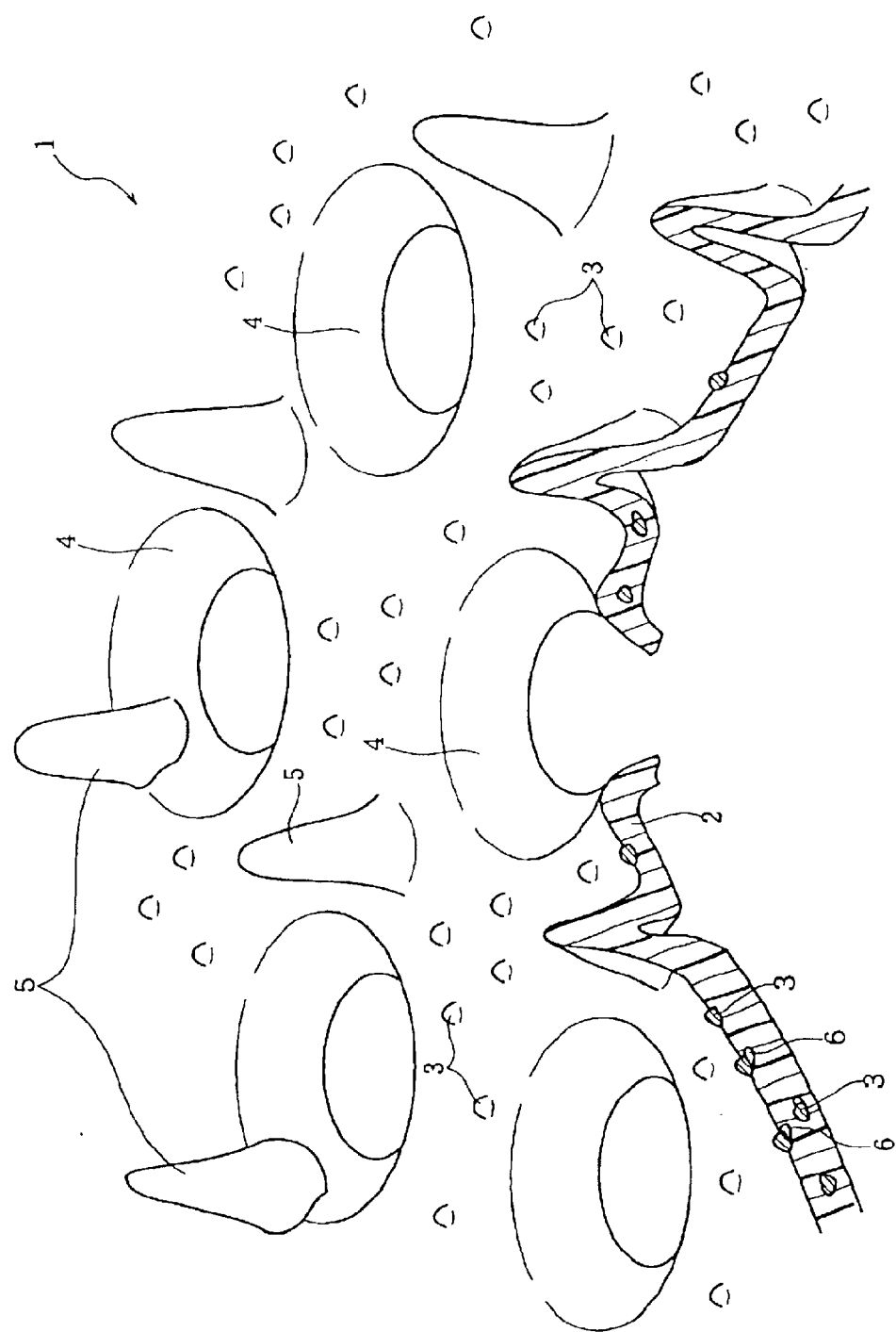
FIG. 1 is a perspective view of a partially enlarged cross section of one embodiment of a top sheet according to the invention.

FIG. 1 is a perspective view of a partially enlarged cross section of one embodiment of a top sheet according to the invention.

As shown in FIG. 1, a top sheet 1 is made of a sheet (film) of a thermoplastic resin 2 containing a number of particles 3 therein. A part of the particles 3 are exposed outside the surface of the top sheet 1. Around the particles 3, formed are micropores 6 that allow water vapor to pass through the top sheet 1. In addition, the top sheet 1 has perforations 4 for allowing excretions to pass through them from the surface side toward an absorbent core (a liquid-absorbing layer) generally disposed below the top sheet 1. Further, the top sheet 1 is formed with a number of protrusions 5 on the surface thereof.

The thermoplastic resin 2 for the top sheet 1 is selected from a group generally consisting of polyethylene, polypropylene, polyvinyl chloride, starch base resins, polyvinyl alcohol, polyurethane, polycaprolactone cellulose esters and blends thereof.

Any materials may be used for the particles 3, provided that they are not deformed under heat and are safe to human bodies. Among these, in order to effectively reduce the sticky feel of the top sheet in wet, they are preferably inorganic particles of at least one type selected from a group consisting of titanium oxide, calcium carbonate, soda ash, gypsum, calcium sulfate, barium sulfate, sodium sulfate, magnesium carbonate, magnesium sulfate, clay, calcium phosphate, silicic anhydride, carbon and talc.

Preferably, the size of the particles 3 falls between 0.1 and 30 µm. If their particle size is larger than the uppermost limit of the defined range, the particles will too much roughen the top sheet, and will give a rough feel to the skin of a wearer, and, as a result, the top sheet will lose a good feel. On the other hand, however, if their size is smaller than the lowermost limit of the defined range, the particles could not well roughen the top sheet to a desired degree and therefore could not well reduce the contact area of the top sheet to the skin of a wearer, and, as a result, the top sheet will have a sticky and stuffy feel. More preferably, the size of the particles 3 falls between 0.1 and 20 µm, even more preferably between 0.5 and 15 µm. It should be noted that the particle size referred to herein is meant to indicate the average of the major diameter of each particle.

Also preferably, the thermoplastic resin to form the top sheet contains from 20 to 150 parts by weight of the particulate material relative to 100 parts by weight of the resin. If the content of the particulate material in the resin is lower than the lowermost limit of the defined range, it is unsatisfactory to reduce a sticky and stuffy feel of the sheet of the resin. On the other hand, however, if the content is larger than the uppermost limit of the defined range, the strength of the sheet will be low.

In the invention, at least two types of particulate material that differ from each other in the mean particle size by at least 9 µm may be added to the thermoplastic resin to form the top sheet 1. In this case, large-size particles shall exclusively roughen the top sheet 1 so that the sheet can have a suitable degree of surface roughness. A part of large-size particles and small-size particles are exposed outside the surface of the top sheet 1 to thereby reduce the filmy feel and the sticky feel of the top sheet.

Regarding the proportion of such different types of particulate material to be contained in the resin, it is desirable that the number of small-size particles is larger than that of large-size particles. It is also desirable that the mass of large-size particles is larger than that of small-size particles.

One embodiment of forming the top sheet 1 that contains two different types of particulate material comprises blending 1-µm particles and 10-µm particles in a ratio of 40:60, followed by adding the resulting mixture to a thermoplastic resin so that the total of these 1-µm particles and 10-µm particles could fall between 20 and 150 parts by weight relative to 100 parts by weight of the thermoplastic resin. The resin containing the particulate material therein is then formed into the top sheet 1.

Figure 2:
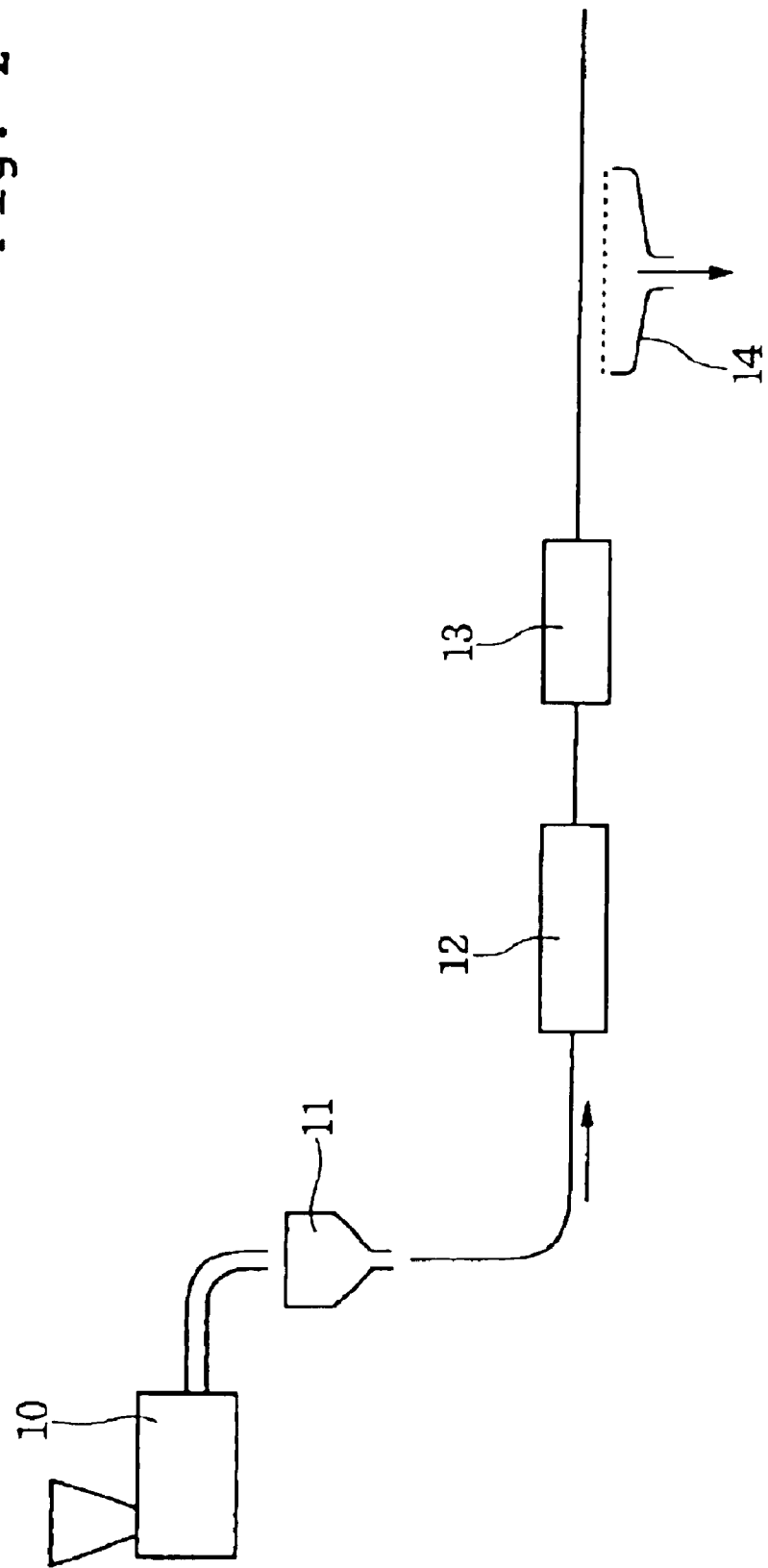
FIG. 2 is a flowchart for producing the top sheet of the invention.

One embodiment of forming the top sheet 1 from the thermoplastic material 2 containing the particles 3 therein is shown in FIG. 2.

Thermoplastic resin pellets are firstly fed into a melt extruder 10 along with particles 3, then the resin pellets are melted under heat therein, and the resin melt is mixed with the particles. The resulting resin mixture is extruded out through a T-die 11, then cooled, and biaxially or monoaxially stretched in a stretcher 12 to be a sheet material (film material). In this process, since the sheet material (film material) for the top sheet 1 is formed from the melt of the resin mixture, the particles 3 hardly drop off from the top sheet to be finally made of the sheet material.

Preferably, the maximum draw ratio in CD (cross direction) and/or MD (machine direction) of the film to obtain the sheet material falls between 1.1 and 5.0 times or so. The film is stretched at least monoaxially, while being so controlled as to have a basis weight of from 20 to 50 g/m$^2$. When being stretched to the preferred draw ratio, the resulting sheet could have the micropores 6 suitably formed around the particles 3 as shown in FIG. 1.

As having such micropores 6, the top sheet 1 is favorable to the absorbent articles, since the excretions having still remained on the top sheet 1 can infiltrate into it through the micropores 6. Accordingly, the surface of the top sheet 1 can be kept nearly dry anytime in use to reduce the unpleasant feel of the wearers. In addition, since the surface of the top sheet 1 can be kept nearly dry in use, the particles 3 exposed outside the top surface 1 are not buried in excretions, and the surface roughness of the top sheet 1 cannot be degraded. However, if the draw ratio of the film to obtain the sheet material for the top sheet 1 is smaller than the lowermost limit of the defined range as above, the micropores 6 could not be formed in the desired manner. If so, the excretions having remained thereon could not well infiltrate into the top sheet 1. On the other hand, if the draw ratio is larger than the uppermost limit of the defined range, the excretions having remained thereon will too much infiltrate into the top sheet 1. If so, the top sheet 1 will feel rather wet. In case where the excretion is the menstrual blood, the top sheet 1 will be much stained in red with the menstrual discharges, and the appearance thereof will be bad. In addition, if the draw ratio is larger than the uppermost limit of the defined range, the sheet material will be subjected to resin orientation, and the thus-oriented sheet material will be hardly perforated in the subsequent perforating step.

In order that the top sheet 1 to be made of the sheet material could have a suitable water vapor transmission rate, it is desirable that the water vapor transmission rate of the sheet material is at most 2000 cc/24 hrs/m$^2$, and more preferably falls between 50 and 1000 cc/24 hrs/m$^2$.

As shown in FIG. 2, the sheet material having been stretched in the stretcher 12 is then embossed under pressure in a needle-embossing unit 13. In the unit 13, the sheet material is mechanically and partially stretched to have a number of the protrusions 5 extending from its surface toward the skin of wearers. The protrusions 5 produce an elastic cushion-like fabric feel. When the sheet material is thus partially stretched, the micropores will be enlarged, and, in addition, the sheet material itself is further stretched and thinned, and becomes soft. However, the top sheet 1 of the invention may not have the protrusions 5.

Preferably, the diameter of the respective protrusions 5 falls between 0.5 and 3.0 mm. Smaller protrusions than those falling within the defined range are difficult to form. Larger protrusions than those falling within the defined range, if formed, will lower the strength of the top sheet, and will deform the perforations 4 which are to be formed through the sheet in the subsequent step. Regarding the shape of the protrusions, they may be cubic, semi-spherical, conical, quadrangular pyramid, polygon-based columnar, or polygon-based pyramidal.

Preferably, the height of the respective protrusions 5 from their bottom falls between 0.05 and 1.0 mm. The height referred to herein is meant to indicate the average of the height of each protrusion. If their height is smaller than the lowermost limit of the defined range, the protrusions 5 will lose their ability to improve the feel of the top sheet to the skin of wearers. On the other hand, if their height is larger than the uppermost limit of the defined range, the protrusions 5 will be readily crushed and could not keep their shape, and therefore will also lose their ability to improve the feel of the top sheet to the skin of wearers.

In view of their feel to the skin of wearers, the distance between the neighboring protrusions 5, 5 preferably falls between 0.1 and 0.5 mm on average, more preferably between 0.2 and 0.3 mm.

The load in compression of the protrusions 5, i.e., a LC value thereof preferably falls between 0.05 and 0.5. The LC value indicates the behavior of the protrusions under compression, and is measured by use of a texture feel tester, Katotec's KES. If their LC value is smaller than the lowermost limit of the defined range, the protrusions will be readily crushed by the pressure of the body of wearers. If their LC value is larger than the uppermost limit of the defined range, their compressive resistance will increase and therefore the protrusions will be hard.

Preferably, the area ratio to form the protrusions 5 is at most 40% of the sheet material. If the area ratio to form the protrusions 5 is larger than the defined range, the strength of the top sheet made of the sheet material will be low. If so, in addition, the top sheet will be broken while it is produced or while used. In order to make the top sheet have a fabric-like soft feel, the area ratio of the protrusions 5 is more preferably controlled to fall between 5 and 30%, even more preferably between 5 and 20%.

The protrusions 5 are not always required to be formed uniformly in the entire surface of the top sheet 1. They may be formed more in the area that may be rubbed against the skin of wearers, for example, in the crotch area than in any other area. For example, the area ratio of the protrusions 5 may be reduced in some degree in the region corresponding to the center region of the absorbent article, and may be increased in some degree in the region corresponding to the opposite side portions thereof.

After the protrusions 5 have been formed thereon, the sheet material is placed on a perforating drum 14 (a perforating member), and vacuumed through holes of the perforating drum 14, whereby the intended perforations 4 that correspond to the holes of the perforating drum 14 are formed in the overall area of the sheet material through it ("vaccumed" means that the sheet material is to be sucked in a vacuum). The perforation density may fall between 50 and 500 perforations/cm$^2$, but preferably between 80 and 250 perforations/cm$^2$. The mean diameter of the perforations preferably falls between 0.5 and 2.0 mm. The mean distance between the neighboring perforations is preferably 0.3 mm or so.

The top sheet 1 of the invention may be coated with a hydrophilic surfactant for promoting infiltration of menstrual discharges thereinto.

Figure 3:
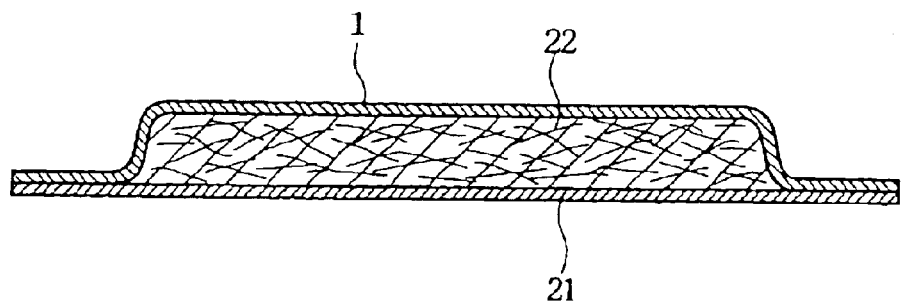
FIG. 3 is a cross-sectional view of one embodiment of an absorbent article of the invention.

FIG. 3 is a cross-sectional view of a sanitary napkin, showing one embodiment of using the top sheet 1 in absorbent articles.

As shown in FIG. 3, the top sheet 1 covers the liquid-receiving surface of an absorbent core (liquid-absorbing layer) 22. The absorbent core 22 may be a liquid-absorbing layer of beaten pulp and the like optionally mixed with SAP (super absorbent polymers). The absorbent core 22 is also wrapped in a liquid-pervious sheet of tissue or the like.

On the back surface of the absorbent core 22, generally provided is a liquid-impervious back sheet 21. The back sheet 21 may be made of, for example, a vapor-pervious but liquid-impervious polyolefin resin film and the like. Around the absorbent core 22, the top sheet 1 and the back sheet 21 are bonded with a hot-melt adhesive or the like.

In the sanitary napkin of the illustrated embodiment, the menstrual discharges applied to the top sheet 1 pass the top sheet 1 through the perforations 4, and are then absorbed by the absorbent core 22.

The top sheet 1 of the invention is applicable to any other absorbent articles, in addition to the sanitary napkin of the illustrated embodiment, for example, to pantiliners, incontinence pads, disposable diapers, etc.

EXAMPLES

The invention is described in more detail with reference to the following Examples, which, however, are not intended to restrict the scope of the invention.

Example 1

50 parts by weight of a particulate material, CaCO$_3$ (having a particle size of 1.8 μm or 15 μm) was added to 100 parts by weight of a thermoplastic resin, polyethylene (LLDPE (linear low-density polyethylene); having a density of 0.197 and a melt flow rate (MFR) of 14), and the resulting mixture was formed into a film, which was then stretched by 1.3 times monoaxially in MD (machine direction) to prepare a sheet material. The sheet material was perforated on a perforating drum by vacuuming it to prepare a top sheet of the invention having a basis weight of 25 g/m$^2$.

MIU (mean coefficient of friction, μ) and MMD (mean deviation of friction coefficient) of the top sheet were respectively measured, for which was used a texture feel tester, Katotec's KES. The sheet not containing the particulate material as a comparative sample was also prepared, and tested in the same manner as herein.

| (Result) | | |
|---|---|---|
| Particle Size: 1.8 μm | MIU = 0.156 | MMD = 0.0142 |
| Particle Size: 15 μm | MIU = 0.138 | MMD = 0.0177 |
| Comparative sample | MIU = 0.185 | MMD = 0.0096 |

From the result thereof, it is understood that the MIU value of the top sheet of the invention is lowered and the MMD value thereof is increased, whereby the top sheet become more slippery. It should be noted that the MIU value is used to indicate the surface lubricating properties of the sheet, and the MMD value is used to indicate the surface roughness of the sheet. This is more significant with the increase in the particle size of the particulate material to be added.

Example 2

50 parts by weight of a particulate material, CaCO$_3$ (having a particle size of 5.4 μm) was added to 100 parts by weight of a thermoplastic resin, polyethylene (LLDPE, having a density of 0.197 and MFR of 14), and the resulting mixture was formed into a film, which was then stretched by 1.3 times monoaxially in MD to prepare a sheet material. Using a pin plate (this has a number of small pins having a diameter of 0.8 mm at regular intervals of 3.5 mm in MD and 4.0 mm in CD) combined with a silicone plate, the sheet material was embossed to make it have a number of protrusions on its surface. The height of the protrusions fell between 0.35 and 0.55 mm. The obtained sheet was then perforated on a perforating drum by vacuuming it to obtain the top sheets of the invention. The LC value (load in compression) and the RC value (rate of recovery) of the non-perforated sheet material and the perforated top sheet were measured, respectively.

| (Result) | | |
|---|---|---|
| Non-perforated sheet material | LC = 0.204 | RC = 45.1 |
| Perforated top sheet | LC = 0.630 | RC = 46.9 |

From the result thereof, it is understood that, in the sheet material having been processed to have protrusions thereon and having been further perforated to have perforations therethrough, the micropores are enlarged and, as a result, the sheet material becomes softer to improve the bulk recovery properties.

As set forth above, the top sheet of the invention has a soft feel and does not have a plastic-like sticky and stuffy feel, though it is made of resin. As the micropores are formed in the top sheet, it is possible to keep the top sheet dry while used, and give no unpleasant feel to the wearers.

In additions from the top sheet produced according to the method of the invention, the particulate material hardly drops off.

While the invention has been described in detail and with reference to specific embodiments thereof, it will be apparent to one skilled in the art that various changes and modifications can be made therein without departing from the spirit and scope thereof.

What is claimed is:

1. A top sheet including a number of perforations for covering a liquid-receiving surface of an absorbent article, wherein;
    the top sheet is formed of a thermoplastic resin containing at least two differently sized particulate materials having a mean particle size in a range of between 0.1 μm and 30 μm, each at least two differently sized particulate materials differing in size from each other by at least 9 μm.
    the top sheet is provided with fine convex portions defined by exposing a part of the particulate material on a body facing surface of the top sheet and a plurality of protrusions extending from the body facing surface, and height of each protrusion from the body facing surface is larger than that of each fine convex portion therefrom, and
    a mean height of the protrusions from the surface of the top sheet is in a range between 0.05 mm and 1.0 mm.
2. The top sheet as set forth in claim 1, wherein the amount of the particulate material is in a range between 20 and 150 parts by weight relative to 100 parts by weight of the thermoplastic resin.
3. The top sheet as set forth in claim 1, which further includes micropores that allow water vapor to pass therethrough.
4. The top sheet as set forth in claim 1, wherein the protrusions are formed by mechanically stretching the top sheet.
5. The top sheet as set forth in claim 1, wherein the particulate material is made of inorganic particles of at least one type selected from a group consisting of titanium oxide, calcium carbonate, soda ash, gypsum, calcium sulfate, barium sulfate, sodium sulfate, magnesium carbonate, magnesium sulfate, clay, calcium phosphate, silicic anhydride, carbon and talc.
6. A top sheet including a number of perforations for covering a liquid-receiving surface of an absorbent article, wherein;
    the top sheet is formed of a thermoplastic resin containing at least two differently sized particulate materials of differently sized inorganic particles having a mean size in a range of between 0.1 μm and 30 μm, each at least two differently sized particulate materials differing in size from each other by at least 9 μm,
    the top sheet includes fine convex portions of the particulate materials partially exposed on a body facing surface of the top sheet and a plurality of protrusions extending from the body facing surface, and a height of each protrusion from the body facing surface is larger than that of each fine convex portion therefrom, and
    a mean height of the protrusions from the surface of the top sheet is in a range between 0.05 mm and 1.0 mm.
7. A top sheet including a number of perforations for covering a liquid-receiving surface of an absorbent article, wherein;
    the top sheet is formed of a thermoplastic resin containing at least two differently sized particulate materials having a mean particle size in a range of between 0.1 μm and 30 μm, each at least two differently sized particulate materials differing in size from each other by at least 9 μm, and
    the top sheet includes micropores formed around the particulate materials, fine convex portions of the particulate materials on a body facing surface of the top sheet, a plurality of protrusions extending from the body facing surface, and a height of each protrusion from the body facing surface is larger than that of each fine convex portion therefrom, and
    a mean height of the protrusions from the surface of the top sheet is in a range between 0.05 mm and 1.0 mm.
8. A top sheet including a number of perforations for covering a liquid-receiving surface of an absorbent article, wherein;
    the top sheet is formed of a thermoplastic resin containing at least two differently sized particulate materials, and
    the top sheet is provided with fine convex portions defined by exposing a part of the particulate materials on a body facing surface of the top sheet and a plurality of protrusions extending from the body facing surface, and a height of each protrusion being in a range between 0.05 mm to 1.0 mm, a mean particle size of said particulate materials being in a range of 0.1 μm to 30 μm, and each at least two differently sized particulate materials differing in size from each other by at least 9 μm.
9. A top sheet including a number of perforations for covering a liquid-receiving surface of an absorbent article, wherein;
    the top sheet is formed of a thermoplastic resin containing at least two differently sized particulate materials having a mean particle size in a range of between 0.1 μm and 30 μm, each at least two differently sized particulate materials differing in size by at least 9 μm,
    the top sheet is provided with fine convex portions defined by exposing a part of the particulate materials on a body facing surface of the top sheet, a plurality of protrusions extending from the body facing surface and a height of each protrusion from the body facing surface is larger than that of each fine convex portion therefrom said fine convex portions including small-size particles defined by exposing a part of a first particulate material having a first particle size and large-size particles defined by exposing a part of a second particulate material having a second particle size which is greater than said first particle size.

10. A top sheet including a number of perforations for covering a liquid-receiving surface of an absorbent article, wherein;

the top sheet is formed of a thermoplastic resin containing at least two differently sized particulate materials having a mean particle size in a range of between 0.1 μm and 30 μm, each at least two differently sized particulate materials differing in size from each other by at least 9 μm, the top sheet is provided with fine convex portions defined by exposing a part of the particulate materials on a body facing surface of the top sheet and a plurality of protrusions extending from the body facing surface of said top sheet, said fine convex portions including small-size particles defined by exposing a part of a first particulate material having a first particle size and large-size particles defined by exposing a part of a second particulate material having a second particle size which is greater than said first particle size, and a height of each protrusion from the body facing surface is larger than that of each small-size particle therefrom, and a mean height of the protrusions from the surface of the top sheet is in a range between 0.05 mm and 1.0 mm.

11. A top sheet including a number of perforations for covering a liquid-receiving surface of an absorbent article, wherein;

the top sheet is formed of a thermoplastic resin containing at least two differently sized particulate materials having a mean particle size in a range of between 0.1 μm and 30 μm, each at least two differently sized particulate materials differing in size from each other by at least 9 μm, and the top sheet is provided with fine convex portions defined by exposing a part of the particulate materials on a body facing surface of the top sheet, a plurality of protrusions extending from the body facing surface and a height of each protrusion from the body facing surface is larger than that of each fine convex portion therefrom said fine convex portions including small-size particles defined by exposing a part of a first particulate material having a first particle size and large-size particles defined by exposing a part of a second particulate material having a second particle size greater than said first particle size, said small size particles and said large size particles being formed by blending said first particulate material and said second particulate material in a ratio of 40:60.

12. A top sheet including a number of perforations for covering a liquid-receiving surface of an absorbent article, wherein;

the top sheet is formed of a thermoplastic resin containing at least two differently sized particulate materials having a mean particle size in a range of between 0.1 μm and 30 μm, each at least two differently sized particulate materials differing in size from each other by at least 9 μm, the top sheet is provided with fine convex portions defined by exposing a part of the particulate materials on a body facing surface of the top sheet and a plurality of protrusions extending from the body facing surface of said top sheet, said fine convex portions including small-size particles defined by exposing a part of a first particulate material having a first particle size and large-size particles defined by exposing a part of a second particulate material having a second particle size which is greater than said first particle size, said small-size particles and said large-size particles being formed by blending said first particulate material and said second particulate material in a ratio of 40:60, and a height of each protrusion from the body facing surface is larger than that of each fine convex portion therefrom, and a mean height of the protrusions from the surface of the top sheet is in a range between 0.05 mm and 1.0 mm.

* * * * *